United States Patent
Meeks et al.

(10) Patent No.: US 7,075,630 B2
(45) Date of Patent: *Jul. 11, 2006

(54) COMBINED HIGH SPEED OPTICAL PROFILOMETER AND ELLIPSOMETER

(75) Inventors: Steven W Meeks, Fremont, CA (US); Rusmin Kudinar, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/873,892

(22) Filed: Jun. 21, 2004

(65) Prior Publication Data

US 2004/0233419 A1    Nov. 25, 2004

Related U.S. Application Data

(63) Continuation of application No. 09/861,280, filed on May 18, 2001, now Pat. No. 6,757,056, and a continuation of application No. 09/818,199, filed on Mar. 26, 2001, now abandoned.

(51) Int. Cl.
*G01N 21/00* (2006.01)

(52) U.S. Cl. ................................................. 356/73

(58) Field of Classification Search ............ 356/73, 356/369, 630, 367, 237.1–237.5, 601, 602, 356/612, 614, 622, 623; 250/559.31, 559.29
See application file for complete search history.

(56) References Cited

U.S. PATENT DOCUMENTS

| | | | |
|---|---|---|---|
| 3,885,875 A | 5/1975 | Rosenfeld et al. | |
| 4,182,259 A | 1/1980 | Garner et al. | |
| 4,332,477 A | 6/1982 | Sato | |
| 4,538,909 A | 9/1985 | Bible et al. | |
| 4,585,348 A | 4/1986 | Chastang et al. | |
| 4,668,860 A | 5/1987 | Anthon | |
| 4,870,631 A | 9/1989 | Stoddard | |
| 4,873,430 A | 10/1989 | Juliana et al. | |
| 5,017,012 A | 5/1991 | Merritt, Jr. et al. | |
| 5,129,724 A | 7/1992 | Brophy et al. | |
| 5,189,481 A | 2/1993 | Jann et al. | |
| 5,196,906 A | 3/1993 | Stover et al. | |
| 5,270,794 A | 12/1993 | Tsuji et al. | |
| 5,293,216 A | 3/1994 | Moslehi | |
| 5,313,542 A | 5/1994 | Castonguay | |
| 5,331,406 A | 7/1994 | Fishbaine et al. | |
| 5,406,082 A | 4/1995 | Pearson et al. | |

(Continued)

FOREIGN PATENT DOCUMENTS

JP    3-221804    9/1991

(Continued)

OTHER PUBLICATIONS

W.C. Leung, W. Crooks, H. Rosen and T. Strand, *An Optical Method Using a Laser and an Integrating Sphere Combination for Characterizing the Thickness Profile of Magnetic Media*, Sep. 1989, IEEE Transaction on Magnetics, vol. 25, No. 5. pp. 3659-3661.

(Continued)

*Primary Examiner*—Tu T. Nguyen

(74) *Attorney, Agent, or Firm*—Caven & Aghevli LLC

(57) ABSTRACT

A system and method for measuring defects, film thickness, contamination, particles and height of a thin film disk or a silicon wafer.

13 Claims, 17 Drawing Sheets

U.S. PATENT DOCUMENTS

| | | |
|---|---|---|
| 5,416,594 A | 5/1995 | Gross et al. |
| 5,446,549 A | 8/1995 | Mazumder et al. |
| 5,463,897 A | 11/1995 | Prater et al. |
| 5,586,101 A | 12/1996 | Gage et al. |
| 5,608,527 A | 3/1997 | Valliant et al. |
| 5,610,897 A | 3/1997 | Yamamoto et al. |
| 5,631,171 A * | 5/1997 | Sandstrom et al. .......... 436/518 |
| 5,633,747 A | 5/1997 | Nikoonahad |
| 5,644,562 A | 7/1997 | de Groot |
| 5,694,214 A | 12/1997 | Watanabe et al. |
| 5,715,058 A | 2/1998 | Bohnert et al. |
| 5,726,455 A | 3/1998 | Vurens |
| 5,748,305 A | 5/1998 | Shimono et al. |
| 5,754,297 A | 5/1998 | Nulman |
| 5,777,740 A | 7/1998 | Lacey et al. |
| 5,798,829 A | 8/1998 | Vaez-Iravani |
| 5,835,220 A | 11/1998 | Kazama et al. |
| 5,864,394 A | 1/1999 | Jordan, III et al. |
| 5,875,029 A | 2/1999 | Jann et al. |
| 5,880,838 A | 3/1999 | Marx et al. |
| 5,903,342 A | 5/1999 | Yatsugake et al. |
| 5,909,276 A | 6/1999 | Kinney et al. |
| 5,951,891 A | 9/1999 | Barenboim et al. |
| 5,978,091 A | 11/1999 | Jann et al. |
| 5,985,680 A | 11/1999 | Singhal et al. |
| 5,986,761 A | 11/1999 | Crawforth et al. |
| 5,986,763 A | 11/1999 | Inoue |
| 5,995,226 A | 11/1999 | Abe et al. |
| 6,028,671 A * | 2/2000 | Svetkoff et al. ............. 356/368 |
| 6,034,378 A | 3/2000 | Shiraishi |
| 6,043,502 A | 3/2000 | Ahn |
| 6,081,325 A | 6/2000 | Leslie et al. |
| 6,088,092 A | 7/2000 | Chen et al. |
| 6,091,493 A | 7/2000 | Stover et al. |
| 6,107,637 A | 8/2000 | Watanabe et al. |
| 6,118,525 A | 9/2000 | Fossey et al. |
| 6,134,011 A | 10/2000 | Klein et al. |
| 6,157,444 A | 12/2000 | Tomita et al. |
| 6,169,601 B1 | 1/2001 | Eremin et al. |
| 6,172,752 B1 | 1/2001 | Haruna et al. |
| 6,201,601 B1 | 3/2001 | Vaez-Iravani et al. |
| 6,248,988 B1 | 6/2001 | Krantz |
| 6,271,916 B1 | 8/2001 | Marxer et al. |
| 6,307,627 B1 | 10/2001 | Vurens |
| 6,353,222 B1 | 3/2002 | Dotan |
| 6,384,910 B1 | 5/2002 | Vaez-Iravani et al. |
| 6,509,966 B1 | 1/2003 | Ishiguro et al. |
| 6,515,745 B1 | 2/2003 | Vurens et al. |
| 6,542,248 B1 | 4/2003 | Schwarz |
| 6,548,821 B1 | 4/2003 | Treves et al. |
| 6,603,542 B1 | 8/2003 | Chase et al. |
| 6,630,996 B1 | 10/2003 | Rao et al. |
| 6,639,662 B1 | 10/2003 | Vaez-Iravani et al. |
| 6,757,056 B1 | 6/2004 | Meeks et al. |
| 6,804,003 B1 * | 10/2004 | Wang et al. ................. 356/369 |
| 6,809,809 B1 | 10/2004 | Kinney et al. |
| 2001/0000679 A1 | 5/2001 | Vaez-Iravani et al. |
| 2001/0030296 A1 | 10/2001 | Ishimaru et al. |
| 2002/0005945 A1 | 1/2002 | Isozaki et al. |
| 2003/0025905 A1 | 2/2003 | Meeks |
| 2004/0169850 A1 | 9/2004 | Meeks |

FOREIGN PATENT DOCUMENTS

| | | |
|---|---|---|
| JP | 04-162215 | 5/1992 |
| JP | 10-227764 | 8/1998 |
| JP | 11-173994 | 7/1999 |
| WO | WO 98/52019 | 11/1998 |

OTHER PUBLICATIONS

Steven W. Meeks, Walter E. Weresin, and Hal J. Rosen, *Optical Surface Analysis of the Head-Disk-Interface of Thin Film Disks*, Jan. 1995, Transactions of the ASME, Journal of Tribology, vol. 117, pp. 112-118.

Steven Meeks, Maxtor and Rusmin Kudinar, *The Next Battleground: Head-Disk Interface*, Mar. 1998, Data Storage, Test & Measurement, pp. 29-30, 34 and 38.

*Laser Scanning Surface Profilometer*, [online], Aug. 1970, [retrieved Jan. 29, 2001], pp. 789-790, Retrieved from the Internet: <URL: http://www.delphion.com/tdbs/tdb?&order=7OC101758.

Meeks, Steven W.: "A Combined Ellipsometer, Reflectometer, Scatterometer and Kerr Effect Microscope for Thin Film Disk Characterization," Machine Vision Applications in Industrial Inspection VIII, Proceedings of SPIE, vol. 3966, 2000, pp. 385-391, XP001085220.

Ikeda, Y. et al., "Characterization of a Disk Texture Transition Zone by USe of an Optical Surface Analyzer," Digests of Intermag., International Magnetics Conference, San Antonio, Apr. 18-21, 1995, p. Ed-2.

European Search Report, Application No. 04028745.0-2204, Apr. 6, 2005.

* cited by examiner

COMBINED HIGH SPEED OPTICAL PROFILOMETER AND ELLIPSOMETER

RELATED APPLICATION

This application is a continuation of patent application Ser. No. 09/861,280, entitled "Combined High Speed Optical Profilometer And Ellipsometer", that was filed on May 18, 2001, now U.S. Pat. No. 6,757,056 and a continuation under 35 U.S.C. §120 to U.S. patent application Ser. No. 09/818,199, entitled "A combined High speed Optical Profilometer and Ellipsometer", that was filed on Mar. 26, 2001 now abandoned.

BACKGROUND OF THE INVENTION

1. Field of the Invention

The present invention is directed toward measuring thin films and defects on silicon wafers, magnetic thin film disks and transparent and coated glass substrates and more particularly toward measuring thin film thickness, and wear, surface roughness, scratches, particles, stains, pits, mounds, surface topography, step heights, and inclusions using a laser directed toward a thin film disk at many angles including non-Brewster's angles of an absorbing layer of the thin film.

2. Description of Background Art

Coated thin film disks are used in a variety of industries including the semiconductor and the magnetic hard disk industry. A computer hard disk (magnetic storage device) is a non-volatile memory device that can store large amounts of data. One problem that the manufacturers of hard disks experience is how to maximize the operating life of a hard disk. When a hard disk fails the data stored therein may be difficult, expensive, or impossible to retrieve. Failure of a hard disk may be caused by defects on the surface of the thin film disk. It is crucial to be able to detect and classify these defects in order to prevent disk drive failure and to control the manufacturing process.

A schematic of a thin film disk used in magnetic storage devices is shown in FIG. 1. It includes a magnetic thin film (layer) 106 which is deposited upon a substrate 108 (typically a NiP plated Al—Mg alloy or glass). The magnetic thin film 106 can be protected by a thin film of carbon 104 (carbon layer), for example, whose thickness is typically 20 to 200 Angstroms (Å). The carbon layer 104 is typically coated with a thin layer (10 to 30 Angstroms) of a fluorocarbon lubricant 102 (lubricant layer). The lubricant layer 102 serves to increase the durability of the underlying carbon layer 104 particularly when the magnetic read/write head contacts the disk, for example when the disk drive is turned off. The hard disk drive industry has been dramatically improving storage capacity by flying the thin film head closer to the surface of the thin film disk. As a result even very small defects can cause a hard drive to fail. These defects may be topographic such as scratches, pits, mounds, or particles or they may be non-topographic such as stains or inclusions. It is necessary to measure all these types of defects to control the disk manufacturing process and improve disk drive manufacturing yield.

A schematic of a semiconductor wafer is shown in FIG. 2. The structure of a semiconductor wafer can be very complex and FIG. 2 shows only one example of a wafer that is undergoing the copper dual damascene process. With reference to FIG. 2, illustrated are a copper layer 201, a second plasma enhanced chemical vapor deposited (PECVD) oxide layer 202, a first PECVD oxide layer 203 and is a silicon substrate 204. The copper layer 201 is polished using a chemical mechanical polishing (CMP) process until only the via holes and copper lines remain. The problem is that the CMP process can leave residual copper, nitride, or CMP slurry on the surface of the wafer. In addition, stains, particles, scratches, and micro-waviness may be present on the polished wafer. It is necessary to detect and measure such defects to control the process of making the wafer. Fewer defects will also mean greater wafer yields at the end of the process.

A problem in the hard disk, semiconductor and photonics industries is to inspect these magnetic disks and wafers for defects such as particles, scratches, pits, mounds, stains, topographic irregularities and inclusions. Conventional techniques to solve these problems are discussed in U.S. Pat. No. 4,674,875, U.S. Pat. No. 5,694,214, U.S. Pat. No. 5,748,305, and U.S. Pat. No. 6,157,444. These patents describe techniques to measure defects using essentially sophisticated scatterometers and reflectometers. None of these systems enables the simultaneous measurement of topographic and non-topographic defects. This invention enables this measurement through the use of a combined reflectometer, scatterometer, ellipsometer, profilometer and Kerr effect microscope.

What is needed is a system and method for examining thin film disks, silicon wafers and transparent wafers that: (1) measures topographic and non-topographic defects; (2) measures the optical profile on these substrates; (3) enables the measurements to be performed simultaneously; (4) measures the thickness of thin films; (4) enables measurement on patterned or unpatterned silicon or photonic wafers; (5) is performed in situ or in line; and (6) measures only a single side of a transparent substrate.

SUMMARY OF THE INVENTION

A system and method for measuring topographic and non-topographic defects and topography on thin film magnetic disks, silicon wafers and transparent substrates. This invention enables the measurement of the height of a defect on a thin film disk or a silicon wafer having a first electromagnetic signal source for generating a first signal toward a first position on the thin film magnetic disk at a first angle, a second electromagnetic signal source for generating a second signal toward the first position on the thin film magnetic disk at a second angle, a spinning device for rotating the object to change the first position, a first position sensitive detector to receive a portion of said first signal that reflects off of the object, and to determine a radial portion of the first signal ($S1r$) and a circumferential portion of said first signal ($S1c$), a second position sensitive detector positioned at a right angle from the first position sensitive detector, to receive a reflected portion of the second signal that reflects off of the object, and to determine a radial portion of the second signal ($S2r$) and a circumferential portion of the second signal ($S2c$).

The system also includes a processor for determining the height of the first position based upon a difference between $S2c$ and $S1c$ that does not include slope information. The system also enables the detection of topographic and non-topographic defects through the measurement of the phase shift of the optical wave. A feature of this invention is its ability to remove a semiconductor pattern from the data and enhance the ability to detect the presence of defects on the patterned silicon or photonics wafer. Several miniaturized embodiments are presented that enable measurement on both sides of disks or wafers.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit(s) of each reference number correspond(s) to the figure in which the reference number is first used.

Figure 1:
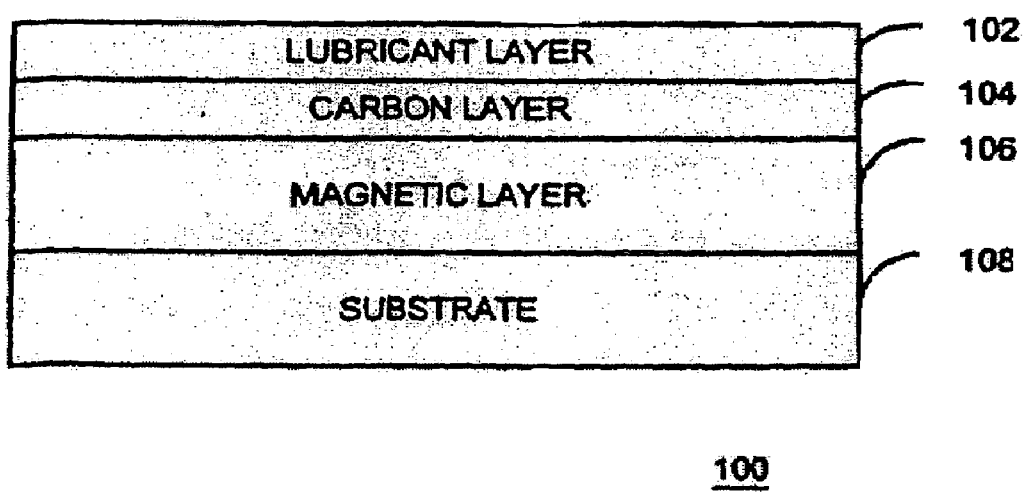
FIG. 1 is an illustration of a thin film that can be measured using an embodiment of the present invention.
Figure 2:
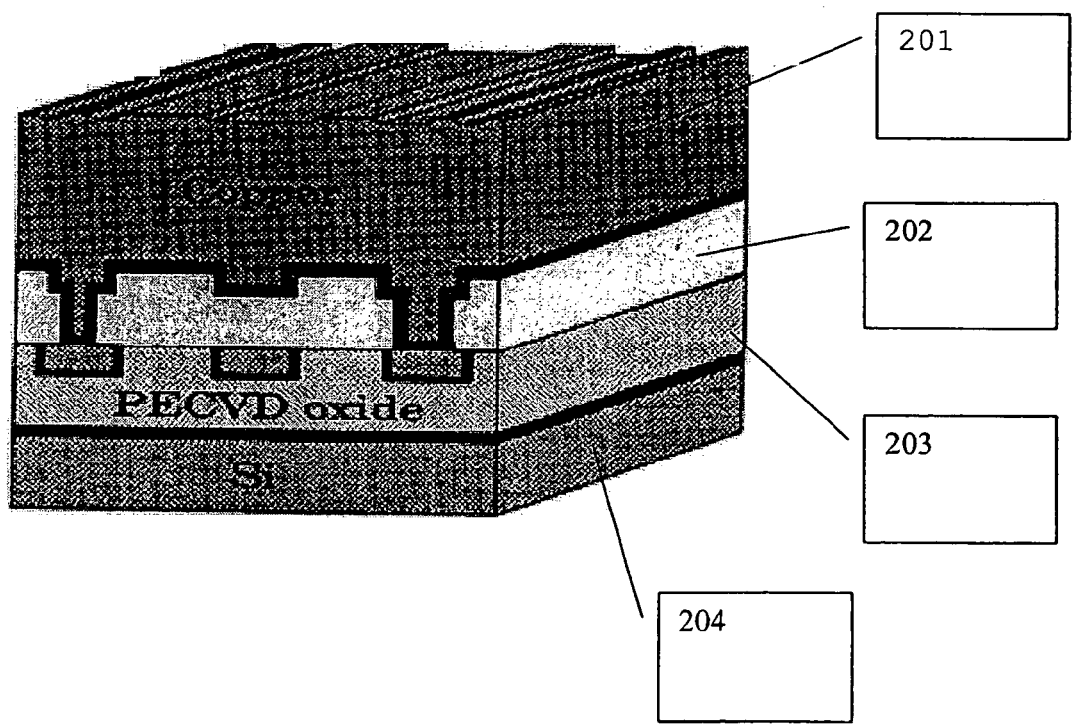
FIG. 2 is an illustration of a semiconductor wafer that can be measured with one embodiment of the present invention.
Figure 3:
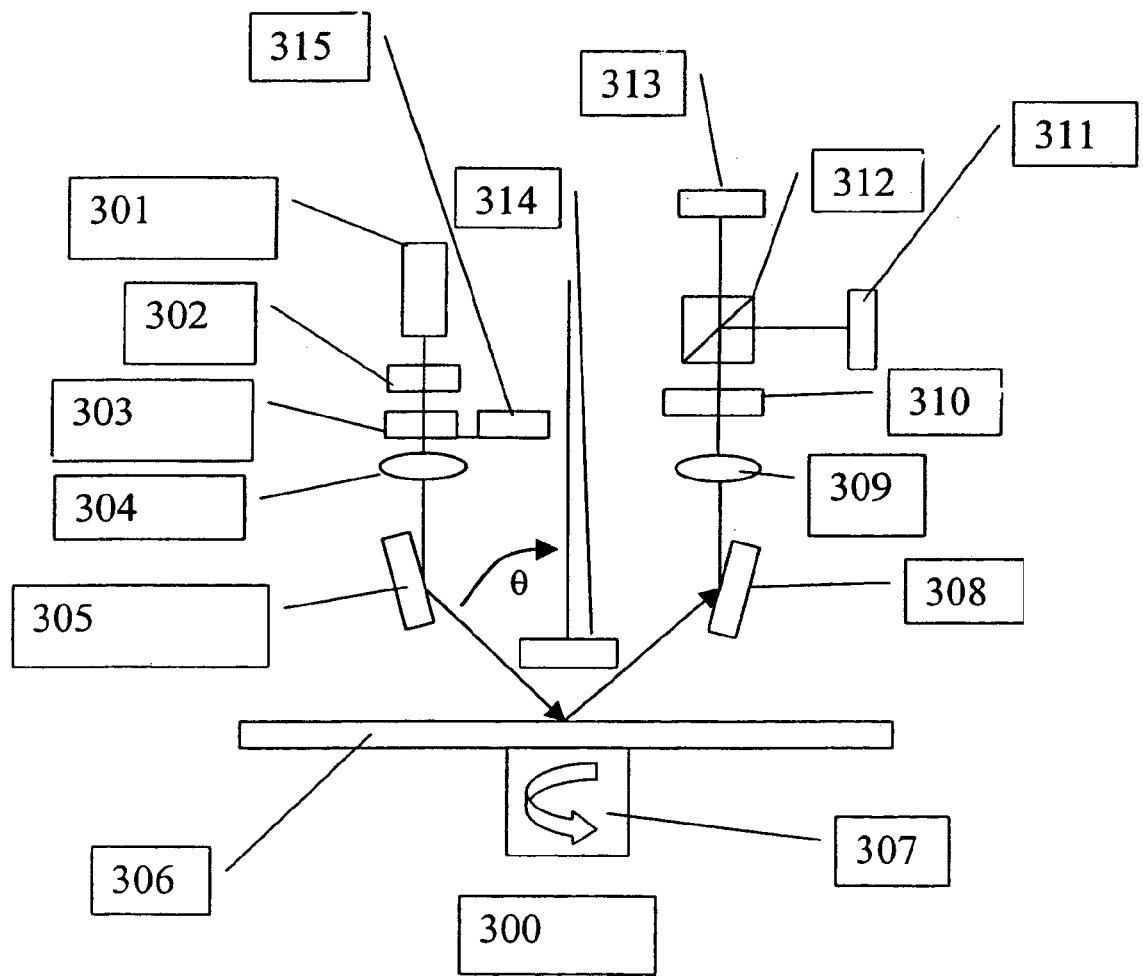
FIG. 3 is an illustration from a side perspective of one half of optical layout of combined ellipsometer and optical profiler according to one embodiment of the present invention.

FIG. 3 is an illustration of an apparatus for measuring properties of the thin film according to an embodiment of the present invention. The apparatus uses a focused laser light signal whose angle of propagation θ (as shown in FIG. 3) can be between zero degrees from normal and ninety degrees from normal.

One embodiment of the apparatus 300 includes a conventional laser diode 301, e.g., RLD65MZT1 or RLD-78MD available from Rolm Corporation, Kyoto, Japan, which has been collimated by Hoetron Corp., Sunnyvale, Calif., e.g., a conventional linear polarizer 302, e.g., made of Polarcor that is commercially available from Newport Corp., Irvine, Calif., a conventional zero order half wave plate 303 that is commercially available from CVI Laser, Livermore Calif., a conventional focusing lens 304 that is commercially available from Newport Corporation, Irvine, Calif., conventional mirrors 305 and 308 available from Newport Corp. Irving, Calif. A collimating lens 309 available from Newport Corp., a zero order quarter wave plate 310 available from CVI Laser Corp., a conventional polarizing beam splitter 312 rotated at 45° to the plane of incidence available from CVI Laser Corp., a pair of conventional quadrant detectors 311 and 313 available from Hamamatsu Corp., Hamamatsu City, Japan, a conventional avalanche photodiode 314 available from Advanced Photonix, Inc., Camarillo, Calif. and a conventional motor 315 available from Maxon Precision Motors, Burlingame, Calif. for rotating the half wave plate 303.

It will be apparent to persons skilled in the art that the apparatus 300 is an embodiment of the present invention and that alternate designs can be used without departing from the present invention. The operation of the apparatus 300 is now described in greater detail.

A laser diode 301 emits an electromagnetic signal toward the thin film disk, silicon wafer, photonics wafer or glass substrate 306. In an embodiment the electromagnetic signal is a light signal having a wavelength of 780 or 655 nanometers (mn) although a wide variety of wavelengths can be used. The angle of propagation of the light signal can be any angle θ between zero and ninety degrees.

Laser diodes are well known to have an internal photodiode to monitor the laser output power. An embodiment of a feedback control circuit to control the optical intensity is to use such a photodiode, which is internal to the laser diode. This photodiode which is internal to the laser diode feeds back a control signal to negative feedback circuitry and by doing so keeps the intensity of the laser at a constant value. Another means of keeping an approximate constant output power of the laser is to control the current of the laser diode, that is, run the diode laser in a constant current mode. The laser diode will exhibit a very slow decrease in output power over a period of months. As long as the scan time is less than 5 or 10 minutes then the optical power output of the laser will remain constant during the scan. The advantage of this technique is its simplicity.

Long-term drifts of the laser output power may be calibrated out of the system by first measuring a standard reflector and using this to normalize the measured signals. The value of the signal is first measured over the standard (known) reflector and then the disk or wafer is measured. If there has been any drift of the standard reflector measurement then all the data is corrected for this amount of drift. As a result long-term drifts may be compensated even when operating in a constant current mode. The emitted light passes through the linear polarizer 302. The linear polarizer 302 improves the linear polarization of the laser light signal.

The linearly polarized light passes through a mechanically rotatable zero order half-wave plate 303. The half wave plate 303 is attached to a miniature motor 315 which allows the polarization to be dynamically rotated between P polarized (parallel to the plane of incidence), S polarized (perpendicular to the plane of incidence) and 45° polarized (between P and S) light. The polarized light passes through a focussing lens 304 and is directed onto a thin film magnetic disk, silicon wafer or transparent substrate 306 by a turning mirror 305. The reflected signal is directed to the detection optics by another turning mirror 308 and recollimated by another lens 309. The scattered component of the signal is detected by an avalanche photodiode 314. The recollimated beam passes through a zero order quarter wave plate 310 that is used to adjust the polarization of the beam so that equal amounts of energy are directed into the quadrant photodetectors 313 and 311. After passing through the quarter wave plate 310 the beam is split by a polarization beam splitter 312 that is rotated by 45° to the plane of incidence. In another embodiment the polarizing beam splitter may be a Wollaston prism or a Glan Thompson or a Rochon prism beam splitter. The split beams are directed onto two quadrant detectors 311 and 313. The quadrant detectors are used to compute the phase shift between the split beams, the reflectivity, the optical profiles in the radial and circumferential directions, and the Kerr rotation (if the film on the substrate 306 is magnetic). The outputs from the quadrant detectors are digitized by a conventional analog to digital converter and directed to the memory of a conventional personal computer. The signals are then analyzed by the personal computer to detect defects, measure topography, and measure stains. The entire optical apparatus 300 is placed upon a stage that moves the apparatus in the radial direction while a motor 307 rotates the sample 306. In this manner the entire surface of the sample 306 may be scanned for defects.

The spindle or motor which rotates the disk at a high rate of speed contains an encoder which produces 1024 pulses as it rotates through 360 degrees, for example. This encoder is used to determine the circumferential positions around the disk. The present invention preferably utilizes a very high-resolution determination of the position around the circumference of the disk. This is accomplished by using a phase locked loop to multiply the encoder signal by a selectable factor. The phase locked loop, which multiplies the 1024 encoder pulses, has the ability to track any velocity jitter in the encoder. This feature allows averaging of repeated revolutions to be done with no loss of lateral resolution. That is, subsequent revolutions lie in phase with one another and when averaged, the resulting image is not smeared by any jitter effect. Averaging is done to improve signal-to-noise ratio.

Figure 4:
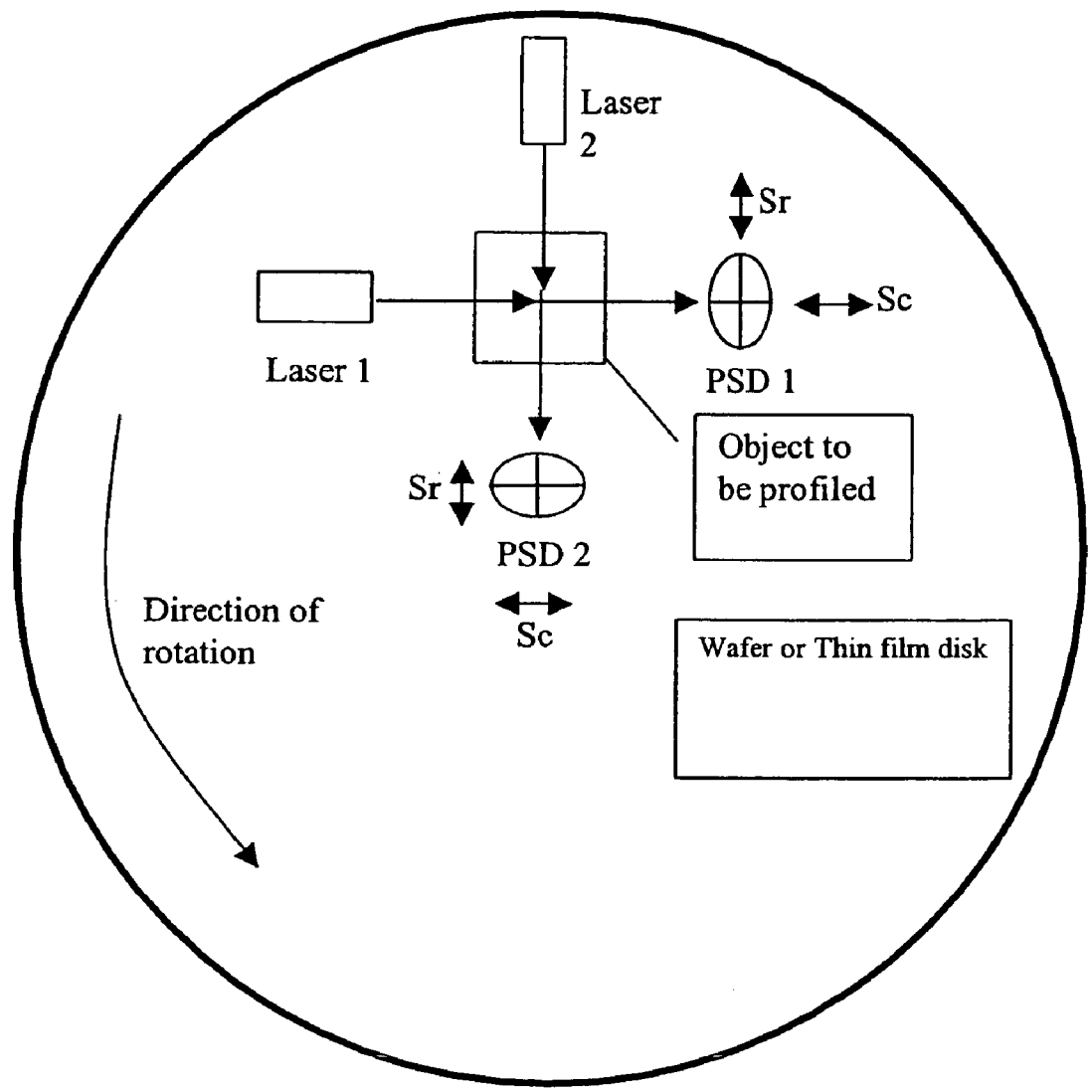
FIG. 4 is a top view of an optical profilometer that measures height or slope according to one embodiment of the present invention.

FIG. 4 shows the top view design of an optical profilometer, which is capable of only measuring the height and directly measuring the height, that is, it can measure the height without measuring the slope. It can also measure the slope of the surface independent of height. This differs from previous optical profilometers that measure both slope and height simultaneously. With such systems the height is obtained from the slope data by integrating the slope information. However, if the slope information is contaminated with height information then the integration will not give the correct surface profile. The problem is to obtain data that contains only height information and not a combination of both slope and height. The design illustrated and described with reference to FIGS. 4–7 accomplishes this by using two lasers and two position sensitive detectors (PSD) oriented at right angles to one another.

The position sensitive detectors (PSD) are quadrant detectors that are oriented as shown in FIG. 4. The PSD's measure the displacement of the beam in the radial and circumferential directions by subtracting the appropriate PSD quadrants. As the laser beam moves along the surface of the object to be measured, the roughness and waviness of the surface cause the laser beam to "wiggle" on the quadrant detector in response to the slope of the surface. The quadrant detector measures this by subtracting the sum of one pair of quadrants from the sum of another pair. For example, referring to FIG. 6, the slope of the surface in the circumferential direction is given by $[(A1+B1)-(C1+D1)]/[A1+B1+C1+D1]$ where the sum of the four quadrants in the denominator is used to normalize for reflectivity differences. At the same time, if the average distance of the surface from the detector changes, then the average position of the beam on the quadrant detector will change. The resulting difference signal in the above equation will register a slope change when in fact a difference in surface height is occurring. The problem is to be able to separate slope changes from height changes. This can be accomplished by considering the slope in the radial direction, which is obtained by referring to FIG. 6 and is given by $[(A1+D1)-(B1+C1)]/[A1+B1+C1+D1]$. The equation for the radial slope measures the "wiggle" of the beam in the radial direction. In the case of the radial slope, if the average distance of the surface from the detector changes then the beam simply moves along the line separating $A1+D1$ from $B1+C1$. As a result the radial slope signal does not change when the surface height changes and the equation for the radial slope records only slope and not height changes.

When the orientation of the laser beam is rotated by 90 degrees (as with laser 2 and PSD 2 in FIG. 4) the behavior of the radial and circumferential slope will reverse. In the case of laser 2 and PSD 2 the circumferential slope equation will record only slope changes and not height changes. On the other hand, for laser 2, the radial slope equation will record both slope and height changes; Since the output beam of both lasers 1 and 2 is positioned at the same location on the surface (as shown in FIG. 4) then it is possible to subtract the radial slope equation from laser 1 and PSD 1 from the radial slope equation from laser 2 and PSD 2. The resulting subtraction will contain only height information and no slope information. It is also possible to obtain the same information by subtracting the circumferential slope equation from laser 1 and PSD 1 from the circumferential slope equation from laser 2 and PSD 2. The radial slope (with no height information) can be obtained by choosing the radial slope equation from laser 1 and PSD 1. The circumferential slope (with no height information) can be obtained by choosing the circumferential slope equation from laser 2 and PSD 2. In this manner it is possible to independently measure surface height variation and slope variation.

Figure 5:
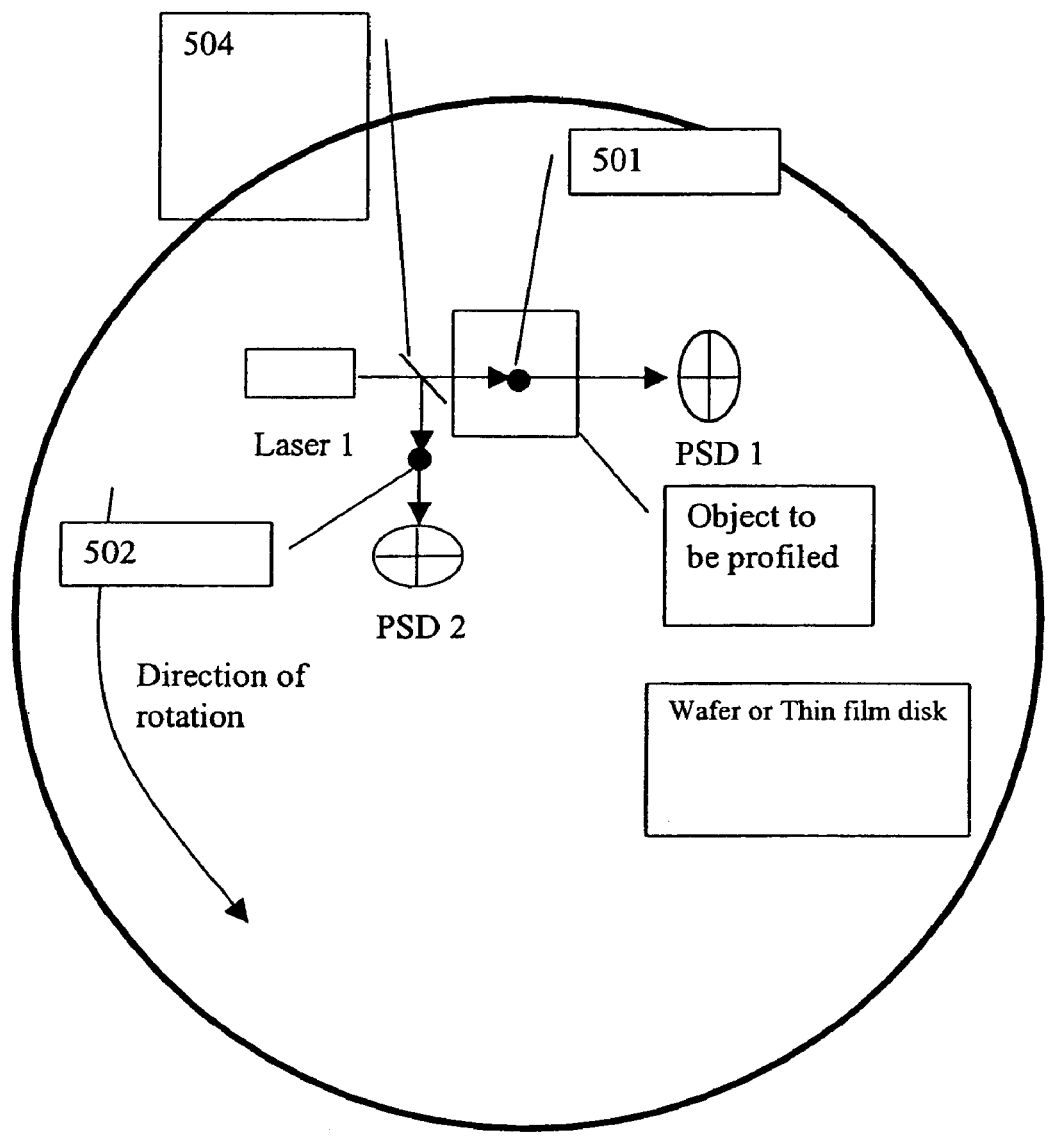
FIG. 5 is a top view of an optical profilometer having a single laser which measures height or slope according to another embodiment of the present invention.

In another embodiment of this optical profilometer, as shown in FIG. 5, a single laser is used and a 50/50 mirror 504 oriented at a compound angle directs a second beam onto the surface to a position labeled 502 on FIG. 5. The beam that passes through the 50/50 mirror 504 is directed onto the surface to a position labeled 501 on FIG. 5. The entire surface of the object to be measured is scanned with both of the beams resulting in at least two images of the surface. The resulting images are stored and digitally shifted so that the resulting images have the object to be profiled at the same x, y location. The resulting shifted images may then be subtracted to give the height profile in the manner described above. The advantage of this embodiment is that it uses only a single laser and fewer optical components and the beam shape of the two beams is identical.

Laser one and PSD 1 nominally measure the signal in the radial, Sr, and the signal in the circumferential, Sc, directions. However, the nature of the PSD results in Sc from laser one and PSD 1 being contaminated with height information, in addition to slope information. Sr from laser 1 and PSD 1 include only slope information. Laser two and PSD 2 also nominally measure the slope in the radial and circumferential directions. However, Sr from laser 2 and PSD 2 measures both slope and height at the same positions as Sr from laser 1 and PSD 1. As a result the true height variation can be obtained by subtracting Sr from laser 2 and PSD 2 from Sr from laser 1 and PSD 1. That is, the slope information is removed when subtracting Sr from PSD 2 from Sr from PSD 1, leaving only the height information.

A similar result can be obtained from subtracting Sc from PSD 2 that only contains slope information. As a result, subtracting Sc from PSD 2 from Sc from PSD 1 gives data containing only height information. The result is a direct measurement of height. The advantages of this technique are that it gives a direct measurement of height and it can be done in a non-contact manner at high speed. This technique can also measure step heights with 90-degree step angles. Conventional systems, which use slope measurements, cannot measure 90-degree step heights.

Figure 6:
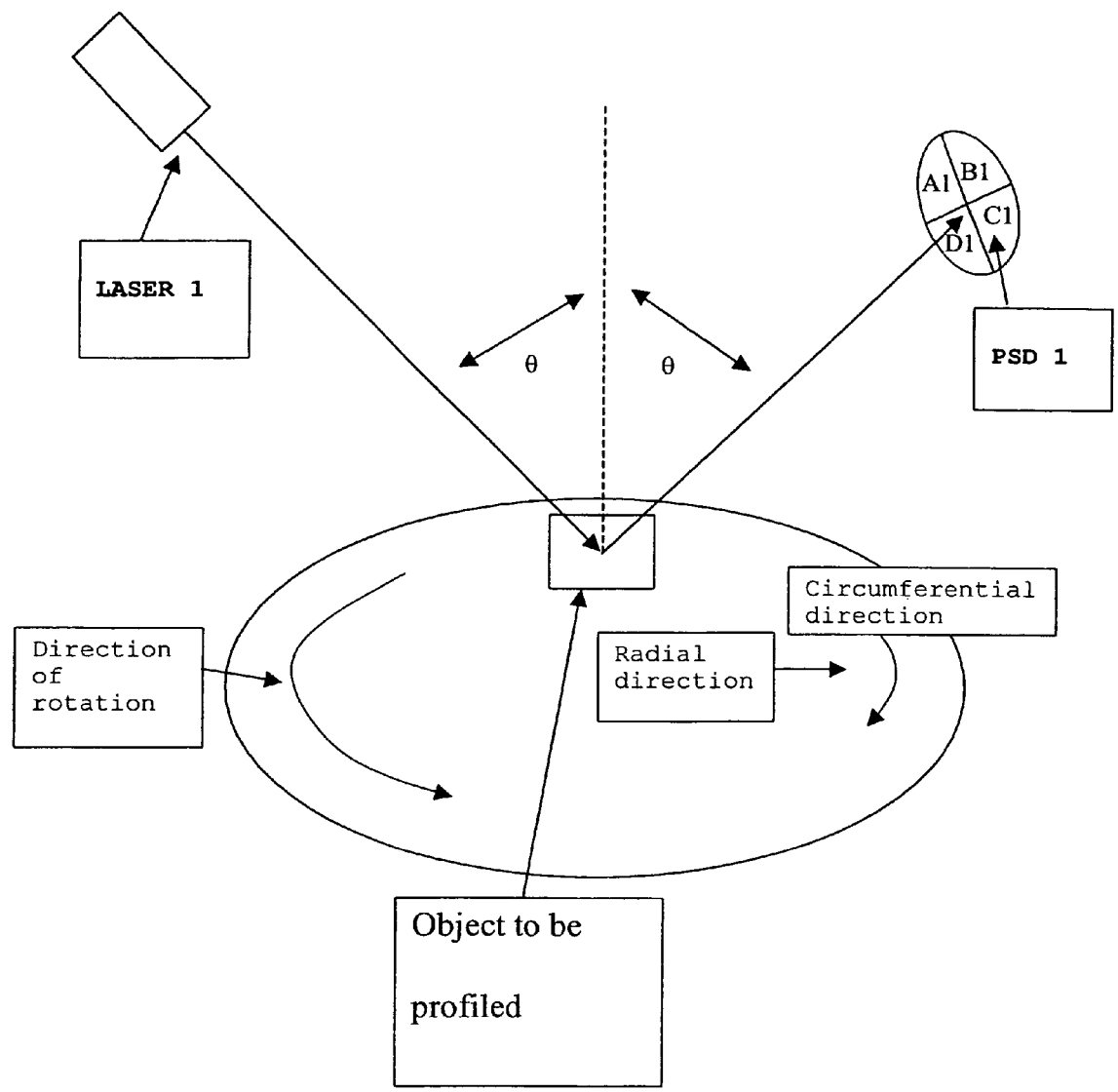
FIG. 6 is a side view of optical profilometer showing laser one and PSD 1 according to one embodiment of the present invention.

FIG. 6 shows the side view design of the optical profilometer. This figure only shows laser 1 and PSD 1 in an effort to easily show the side view design. In FIG. 6. one can see that the optical profilometer is positioned above a thin film disk or wafer and is translated in the radial direction while the disk or semiconductor wafer is rotated.

Figure 7:
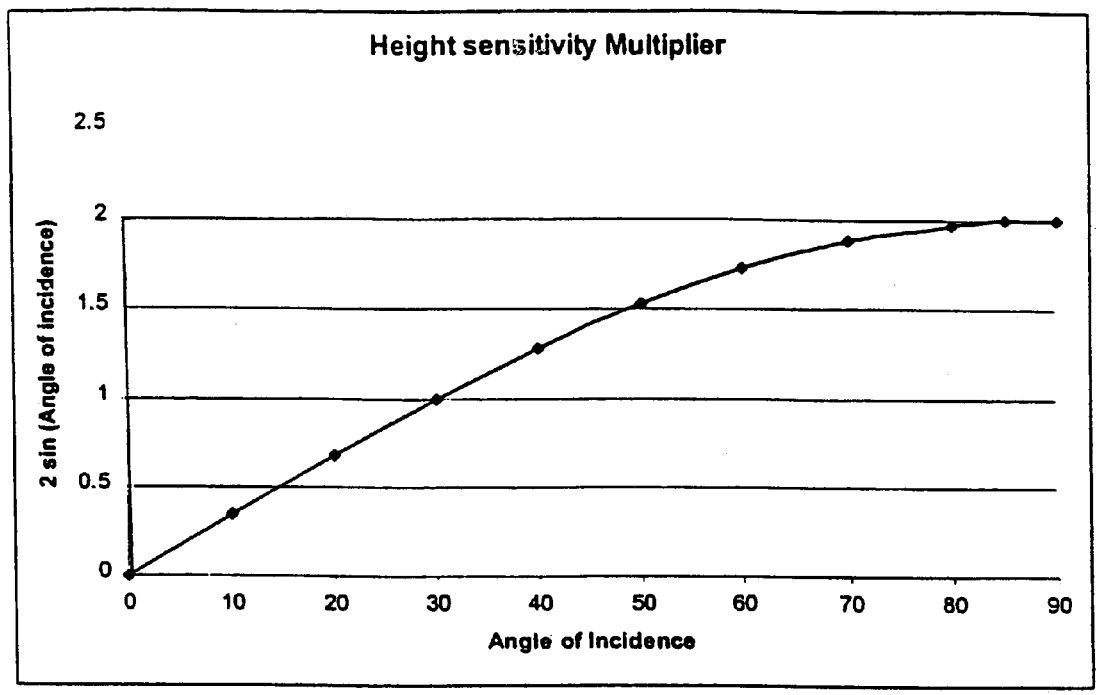
FIG. 7 illustrates the height sensitivity multiplier as a function of angle of incidence (theta) according to one embodiment of the present invention.

The angle of incidence ($\theta$) shown in FIG. 6 can be chosen for the particular application. Any angle of incidence can be chosen except normal incidence, where the PSD's would have no height sensitivity. For an application that involves transparent substrates one could choose angles greater than 45 degrees in order to increase the reflection signal from the surface. As the angle of incidence increases, the height sensitivity also increases by the factor $2*\sin(\theta)[\sin(\theta)/\cos^2(\theta)]$. A plot of this factor is shown in FIG. 7. This suggests that an angle of incidence greater than or equal to approximately 60 degrees would be optimal, although not necessary. At angles greater than 60 degrees the sensitivity will increase and the signal from a transparent surface will increase. This invention requires that the focused spot sizes of the two lasers be substantially identical and that the laser spots overlap as closely as possible.

A problem in the magnetic recording industry is to inspect thin film disks for defects at the final test step of the manufacturer of disks. The manufacturers of thin film disks require that both sides of the thin film disk be inspected simultaneously. The problem is that the clearance between the disk and the chuck (which holds the disk) is only 1" or less (see FIG. 13, 1304). This requires that the optics be miniaturized in order to fit in the small space between the disk and the chuck (see FIG. 13). A solution to this problem can be obtained by using the optical designs in FIGS. 8, 9, 10, and 11. These designs have several key improvements over conventional systems, which allow the design to be miniaturized without compromising the performance of the device. First of all the design uses the internal feedback photodiode, which is contained within the laser diode 801, to achieve stabilization of the DC level of the optical signal. Secondly, the angle of incidence, $\theta$, is adjusted to reduce the height of the instrument so that it will fit within the 1" space requirement. Thirdly, the surface topography measurement capability feature of the instrument is incorporated within the phase/specular detectors 808 and 809 shown in FIGS. 8 and 9. The position sensitive detectors 808 and 809 (quadrant detectors) serve as both phase detectors, specular detectors, and topography measurement detectors.

Figure 8:
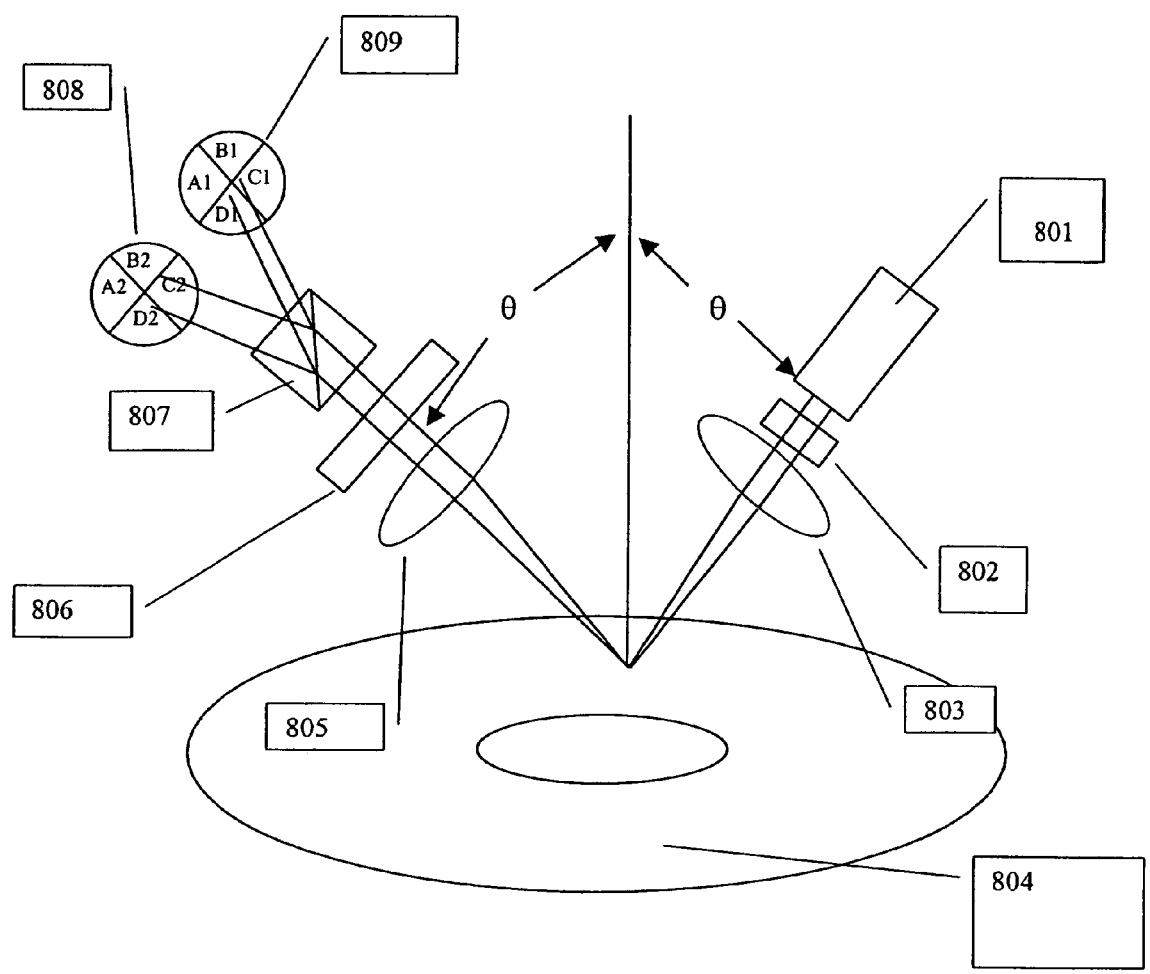
FIG. 8 is an illustration of a miniature optical surface analyzer according to one embodiment of the present invention.
Figure 9:
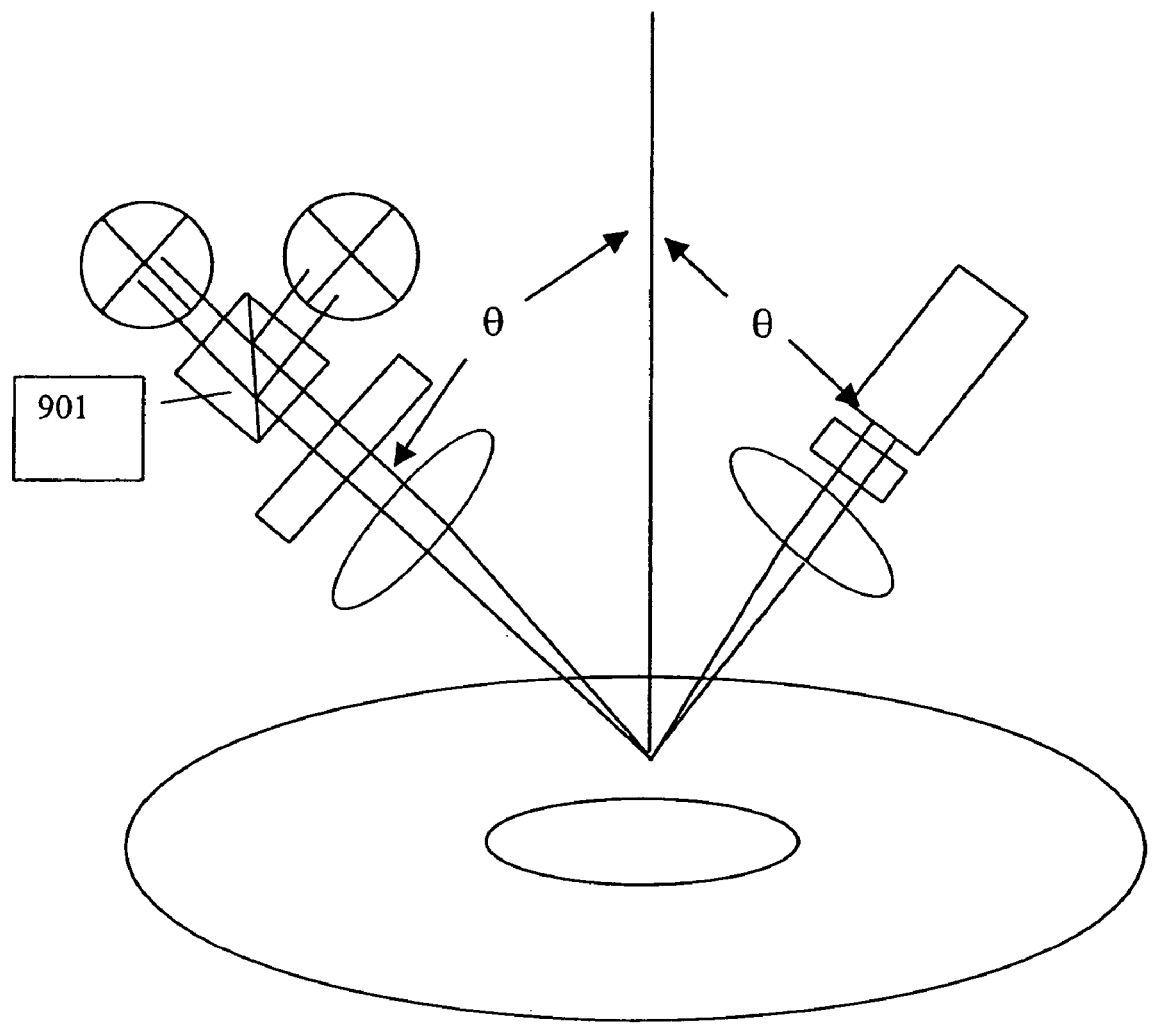
FIG. 9 is an illustration of a miniature optical surface analyzer according to another embodiment of the present invention.
Figure 10:
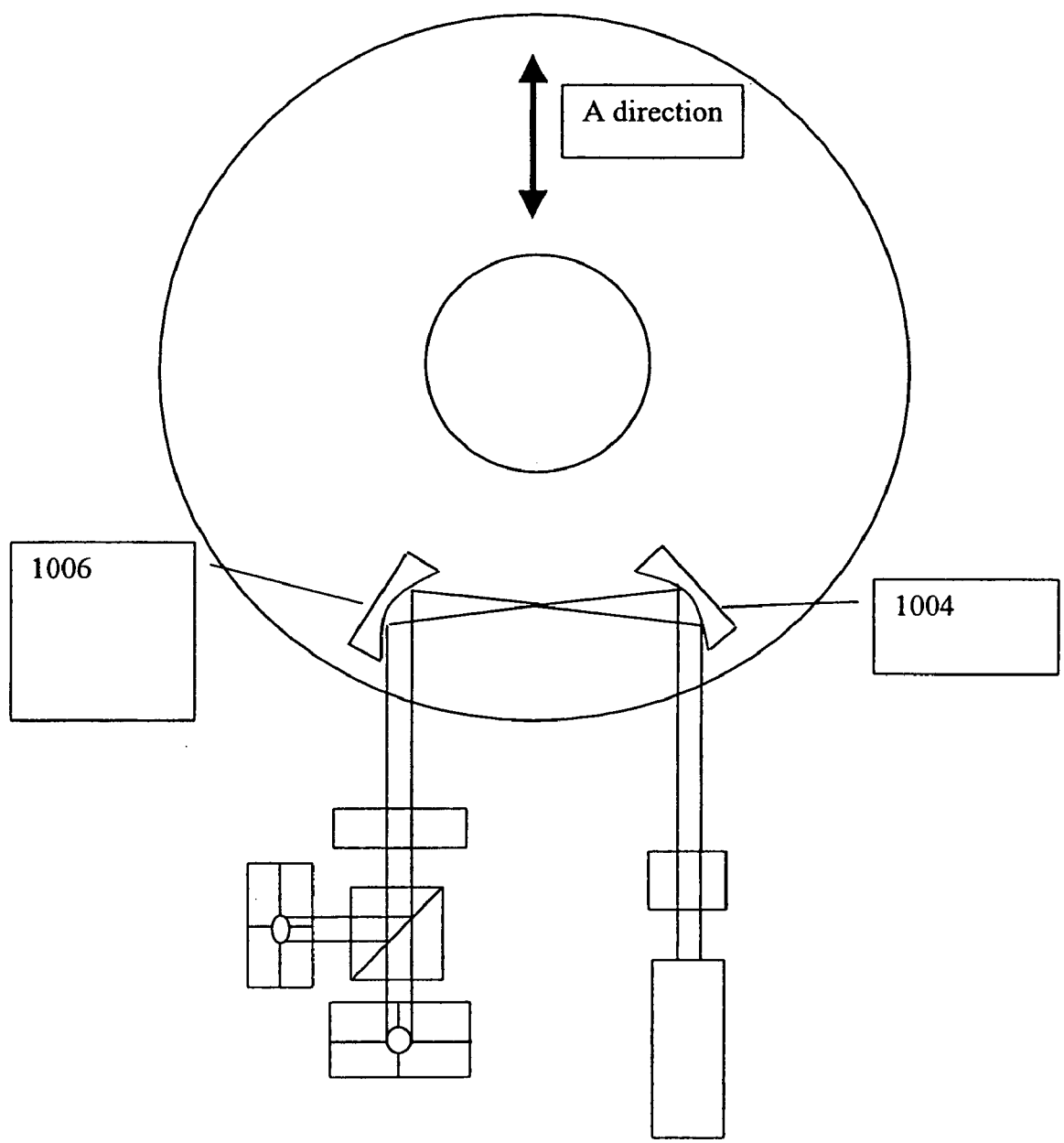
FIG. 10 is an illustration from a top view perspective of a miniature surface analyzer according to another embodiment of the present invention.
Figure 11:
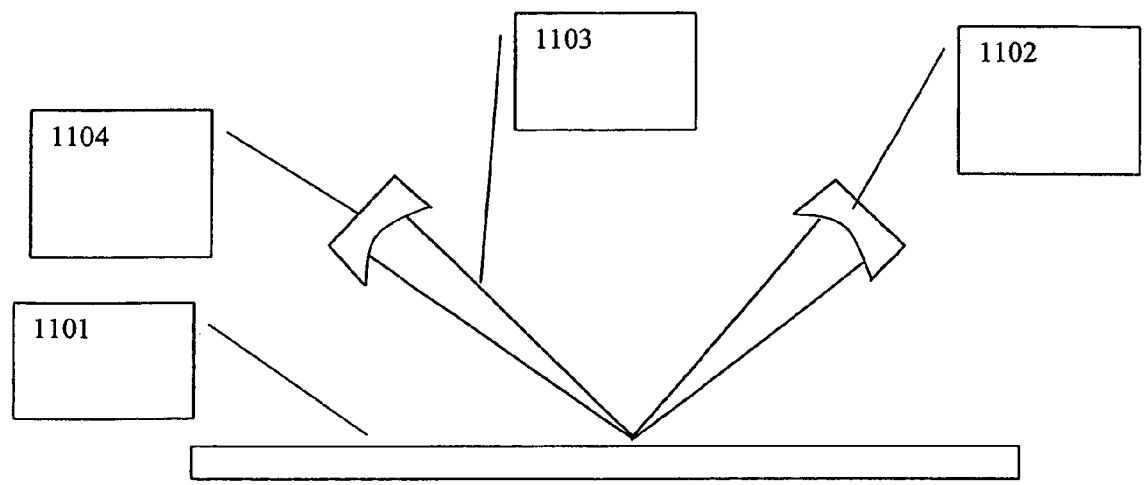
FIG. 11 is an illustration from in the direction identified as "A" of the miniature surface analyzer illustrated in FIG. 10.
Figure 12:
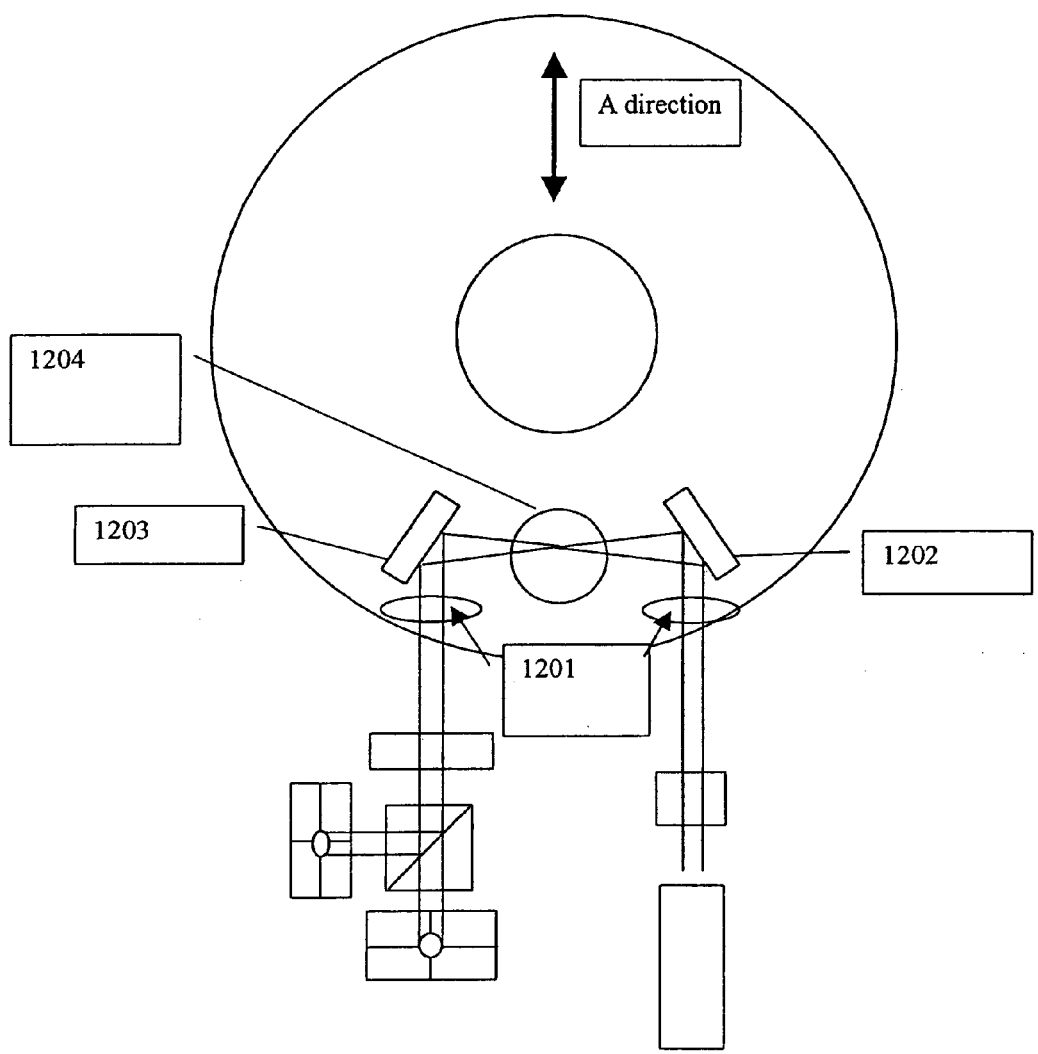
FIG. 12 is an illustration from a top view perspective of a miniature surface analyzer according to another embodiment of the present invention.

Fourthly, the size may be decreased by using a polarizing beam splitter 901 as shown in FIG. 9 instead of a Wollaston prism 807 as shown in FIG. 8. The polarizing beam splitter 807 or Wollaston prism 901 is rotated at 45° with respect to the plane of incidence. Another embodiment of this invention can use a beam splitter that splits the beam into non-orthogonal components, which will be discussed in a subsequent section. Fifthly using two spherical mirrors 1004 and 1006 to direct the beam onto the disk as shown in FIG. 10 will diminish the size in the lateral dimension. The mirrors 1004 and 1006 are adjusted at a compound angle as shown in FIG. 10. This is also shown in FIG. 11 which is a view of FIG. 10 along the "A" direction, where the mirrors that are at a compound angle are 1102 and 1104. These mirrors direct the beam 1103 onto the disk or wafer 1101. In addition to directing the beam onto the disk the spherical mirrors also focus the beam to a small spot. An alternative embodiment to the use of a spherical mirror is to use flat mirrors 1202 and 1203 in combination with focussing lenses 1201 as shown in FIG. 12. Also shown in FIG. 12 is a silicon photodetector or avalanche photodiode 1204, which is positioned above the point where the beam strikes the disk. This element enables the detection of submicron particles. The avalanche photodiode 1204 is available from Advanced Photonix, Inc., Camarillo, Calif.

Referring to FIG. 8, the laser beam from the diode laser 801 passes through a linear polarizer 802, and a focussing lens 803 and then strikes a disk or wafer 804. Upon reflecting from the surface the beam passes through a recollimating lens 805, a quarter wave plate 806, and through a polarizing beam splitter such as Wollaston prism 807 which is rotated at 45° to the plane of incidence and onto two quadrant detectors 808 and 809.

Referring to FIG. 8, the specular signal is obtained by summing the signals from position sensitive detector 1 809 with the sum of position sensitive detector 2, 808 times a constant $\kappa$:

$$\text{Specular signal} = (A1+B1+C1+D1) + \kappa*(A2+B2+C2+D2)$$

The phase shift between the two split beams of the wave (PS) can be obtained by subtracting the sum of the elements of detector 1 809 from those of detector 2, 808 times a constant K:

$$PS = (A1+B1+C1+D1) - K*(A2+B2+C2+D2)$$

Referring to FIG. 8 detector 1, 809, the slope in the circumferential direction (SCD) is given by:

$$SCD = [(B1+C1)-(A1+D1)]/(A1+B1+C1+D1)$$

The slope in the radial direction (SRD) is given by:

$$SRD = [(A1+B1)-(C1+D1)]/(A1+B1+C1+D1)$$

The topography in the circumferential or radial direction is obtained by integrating the slope in the circumferential or radial direction, respectively. The slope signals can also be obtained from detector 2, 808 with the same equations as shown above except for substituting 2 for 1.

Using the designs in FIGS. 8, 9, 10 and 12 will allow the measurement of sub-micron scratches, particles, stains, pits, mounds, handling damage, wear of the carbon layer, outside diameter damage and contamination. This design can also measure the longitudinal Kerr effect by a measurement of the Kerr rotation angle. The advantages of this design are its small size which is made possible by detectors which combine the measurement of phase shift, specular reflectivity, radial and circumferential slope, and scattered light.

Figure 13:
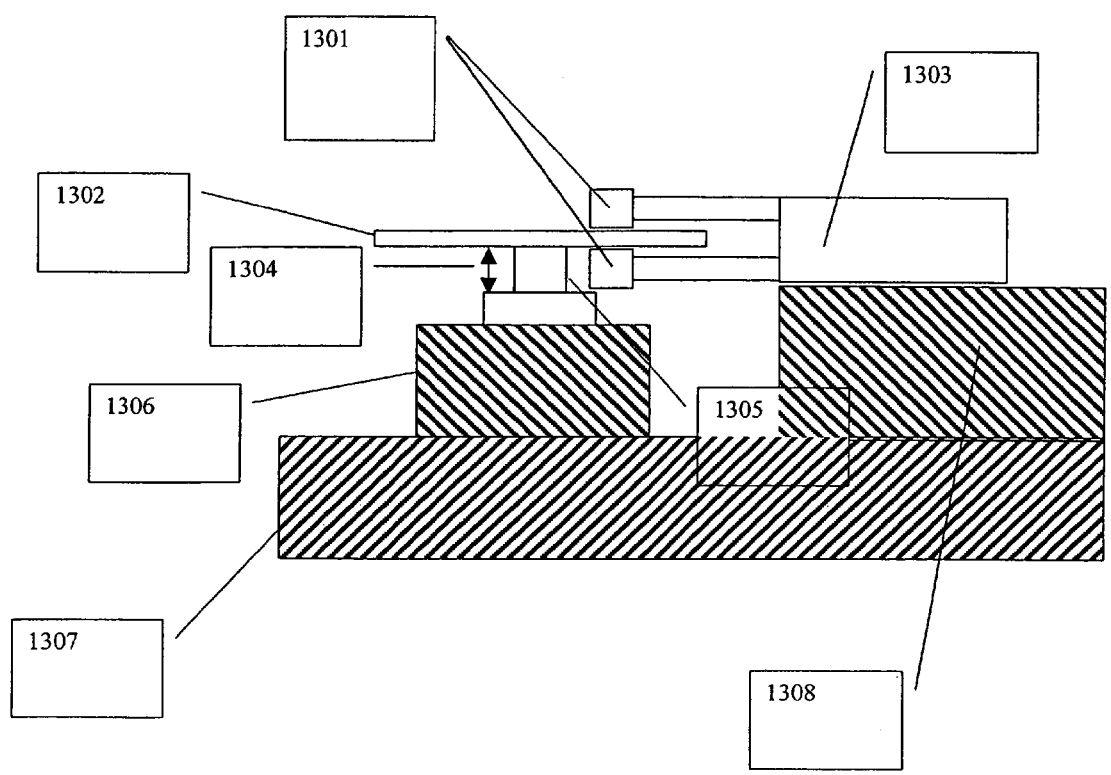
FIG. 13 is an illustration of a final test spindle having dual miniature optical heads and stepper motor according to one embodiment of the present invention.

One embodiment of a miniature optical design that may be mounted on the top and bottom of a thin film disk 1302 is shown in FIG. 13. The resulting combination is translated over the surface of the disk with a stepper or DC servomotor driven stage 1308. A spindle motor 1306 rotates the disk while the optics 1301 is translated in the radial direction so that 100% of the surface of the disk may be measured for defects. The entire apparatus is mounted on a baseplate 1307. The electronics package is located above the stepper motor 1303. The disk is placed upon a vacuum chuck 1305 that is rotated at a high rate of speed.

Figure 14:
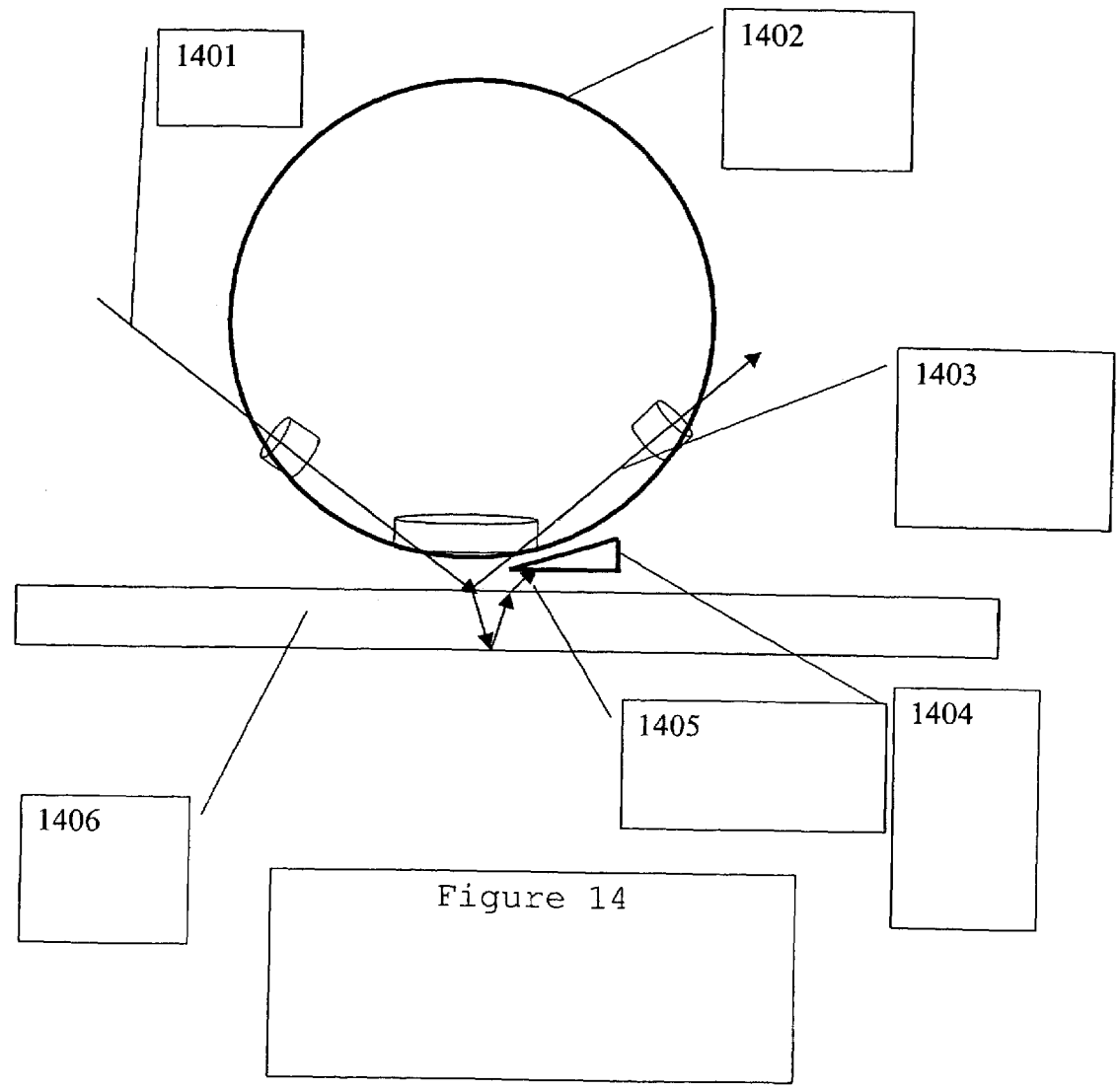
FIG. 14 is an illustration of a spatial filter for blocking bottom surface reflection from a glass or transparent substrate according to one embodiment of the present invention.

A problem in the inspection of transparent glass substrates 1406 and other transparent objects is to separate the signal from the top and the bottom surface. This can be accomplished by the use of a spatial filter 1404 that blocks the signal from the bottom surface 1405 and does not affect the top surface reflection 1403. FIG. 14 shows this in the optical design of the Optical Surface Analyzer (OSA). The incoming optical beam is 1401.

The spatial filter 1404 is in the shape of a small wedge that is attached to the bottom surface of the integrating sphere 1402. The location of the spatial filter is adjusted to just block the bottom surface reflection 1405 and not to interfere with the top surface reflection 1403. This invention allows one to separate information from the top and bottom surface of a transparent glass disk or wafer 1406. This invention also works with any transparent medium such as lithium niobate, fused silica, photoresist, and other transparent oxides.

An alternative design does not require the spatial filter to be attached to the bottom of the integrating sphere. For example, the integrating sphere may be omitted and the spatial filter may be attached to any other point on the optical body. The spatial filter should be located near enough to the transparent substrate so that the reflections from the top and bottom surface are separated in the lateral plane. In this manner it is possible to intercept the bottom surface reflection with the spatial filter and leave the top surface reflection unaffected.

A problem in the measurement of semiconductor wafers is the detection of defects caused by the CMP (Chemical Mechanical Polishing) process. These defects can be residual copper, nitride, slurry, particles, scratches and stains. The measurement is complicated by the fact that the semiconductor wafers have a complex pattern on their surface. A goal is to separate the defects from the complex pattern of semiconductor devices on the surface of the semiconductor wafer. This can be accomplished by the design shown in FIG. 15. The device consists of a means for measuring the phase shift between two mixed polarization components of the incident beam, where the two mixed polarization components are comprised of both P and S polarization components relative to the plane of incidence, and a means to measure the topography of the surface. The device consists of a laser 1501 and a polarizer 1502. The laser is directed onto a focussing lens 1503 and onto a mirror 1504 that directs the beam onto a wafer or disk 1505 that may be rotated by a motor 1506. The reflected beam is directed by another mirror 1507 onto a collimating lens 1508 and through a quarter wave plate 1509. The signal passing through the quarter wave plate is directed onto a polarizing beam splitter 1511 that is oriented at 45° to the plane of incidence. The split beams are measured with two photodetectors 1510 and 1512. The phase shift of the incident beam is proportional to the difference in the amplitudes of photodetectors 1510 and 1512.

When the phase shift between the split beams is measured it is found that the orientation of the semiconductor pattern lines will have a substantial effect on the measured phase shift. What is desired is to remove the semiconductor pattern and enhance the defects.

Figure 15:
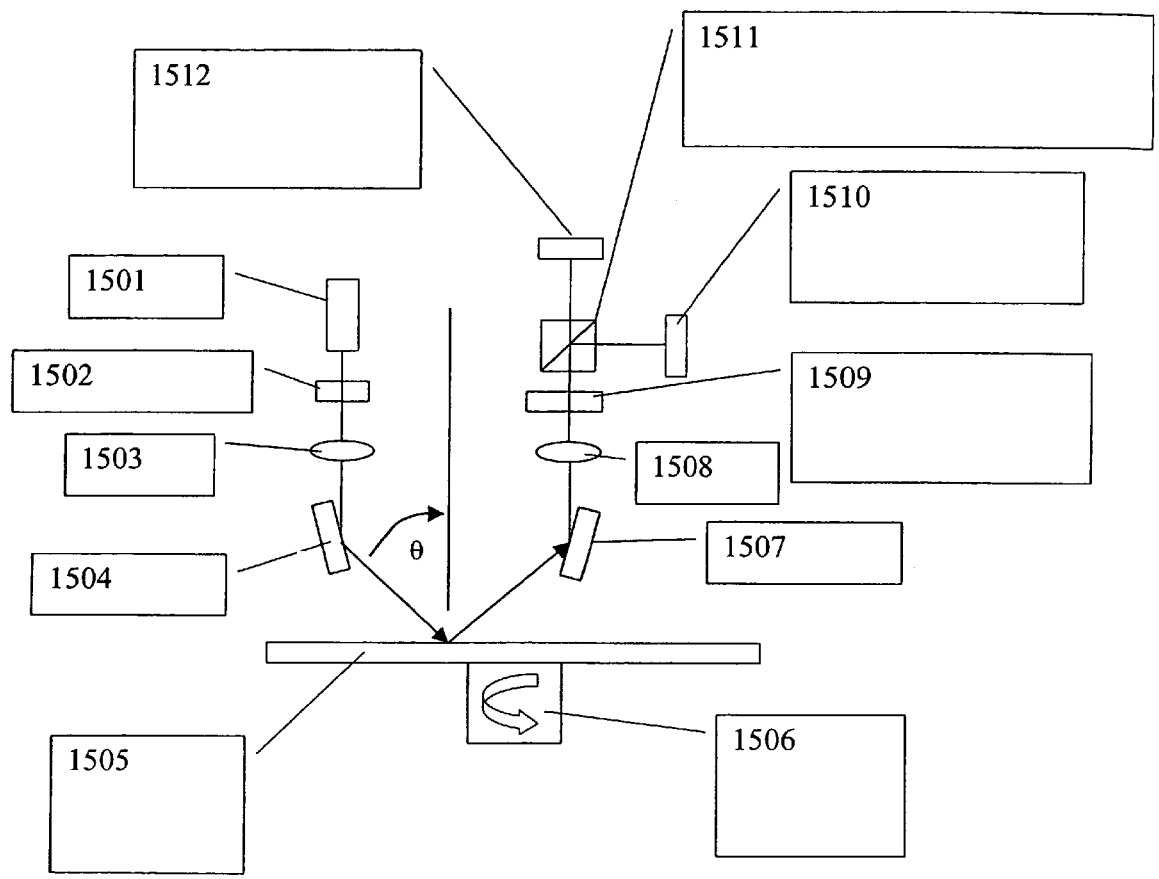
FIG. 15 is an illustration from a side view perspective of one half of optical layout of combined ellipsometer and optical profiler according to one embodiment of the present invention.
Figure 16:
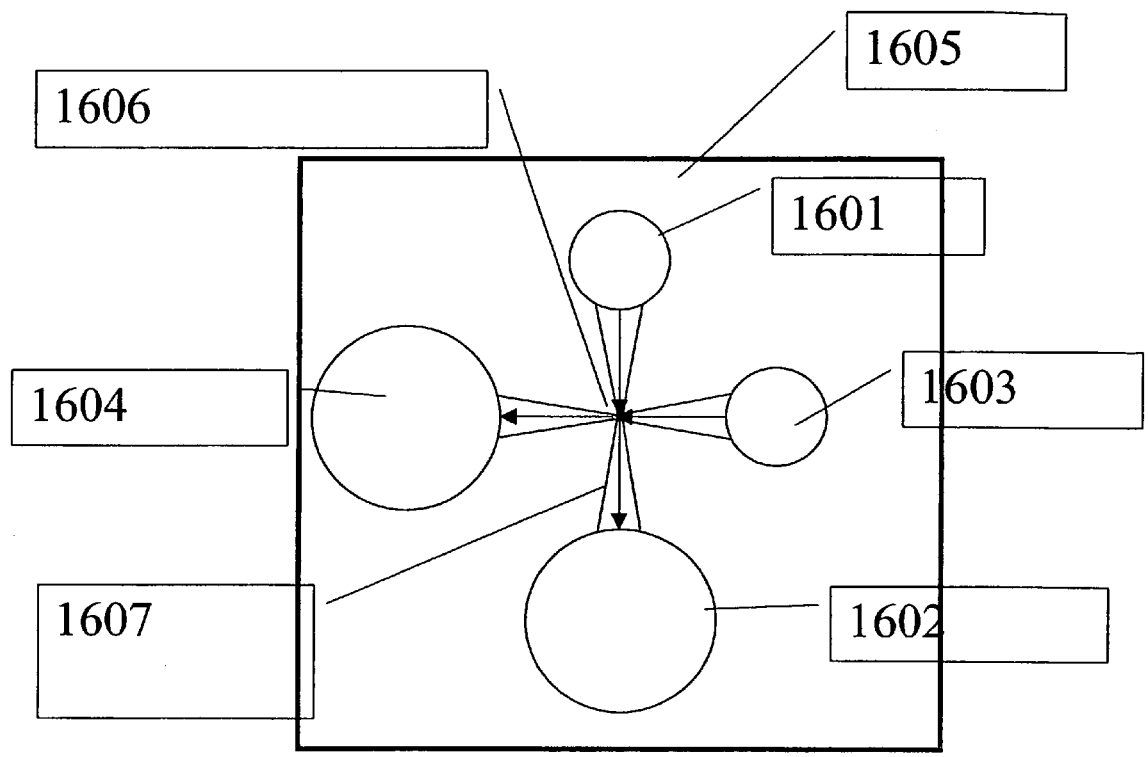
FIG. 16 is an illustration from a top view perspective of a combined ellipsometer and optical profilometer according to one embodiment of the present invention.

A means to accomplish this is to image the wafer with two orthogonal beams as shown in FIG. 16. An optical path shown in FIG. 15 generates each of the beams shown in FIG. 16. Laser one 1601 and detector one 1602 in FIG. 16 generate a phase shift image of the surface that has one particular amplitude due to the orientation of the semiconductor pattern lines. Laser two 1603 and detector two 1604 have a particular amplitude pattern that is identical in lateral shape but opposite in amplitude to that generated by laser one 1601 and detector one 1602. This is because the orientation of the optical beams of lasers one and two are orthogonal with respect to the orientation of the pattern lines. As a result, what is generated are two phase shift images of the surface of the semiconductor that have opposite amplitude phase shift signals from the semiconductor pattern lines. If these two images are added together then the semiconductor pattern will be greatly attenuated.

Defects, on the other hand, do not change phase shift in the two orthogonal beams and as a result when the two orthogonal images are added the defects increase in amplitude and the semiconductor pattern diminishes in amplitude. Defects do not have opposite phase shift amplitudes since most defects are isotropic in nature and do not have the strong anisotropy associated with semiconductor pattern lines. This technique effectively enhances the defect signals and diminishes the semiconductor pattern signal. The focussed beams 1607 cross at point 1606. The entire device is contained within housing 1605.

This invention has the additional advantage that it can simultaneously measure the topography of the surface. In the preferred embodiment the angle of incidence (θ) shown in FIG. 15 is at approximately 60°. Larger or smaller angles of incidence may be used depending upon the application. For example, a larger angle of incidence may be used if a transparent substrate is to be examined. This would be advantageous since a transparent substrate will give a larger signal from the top surface with a greater angle of incidence.

Figure 17:
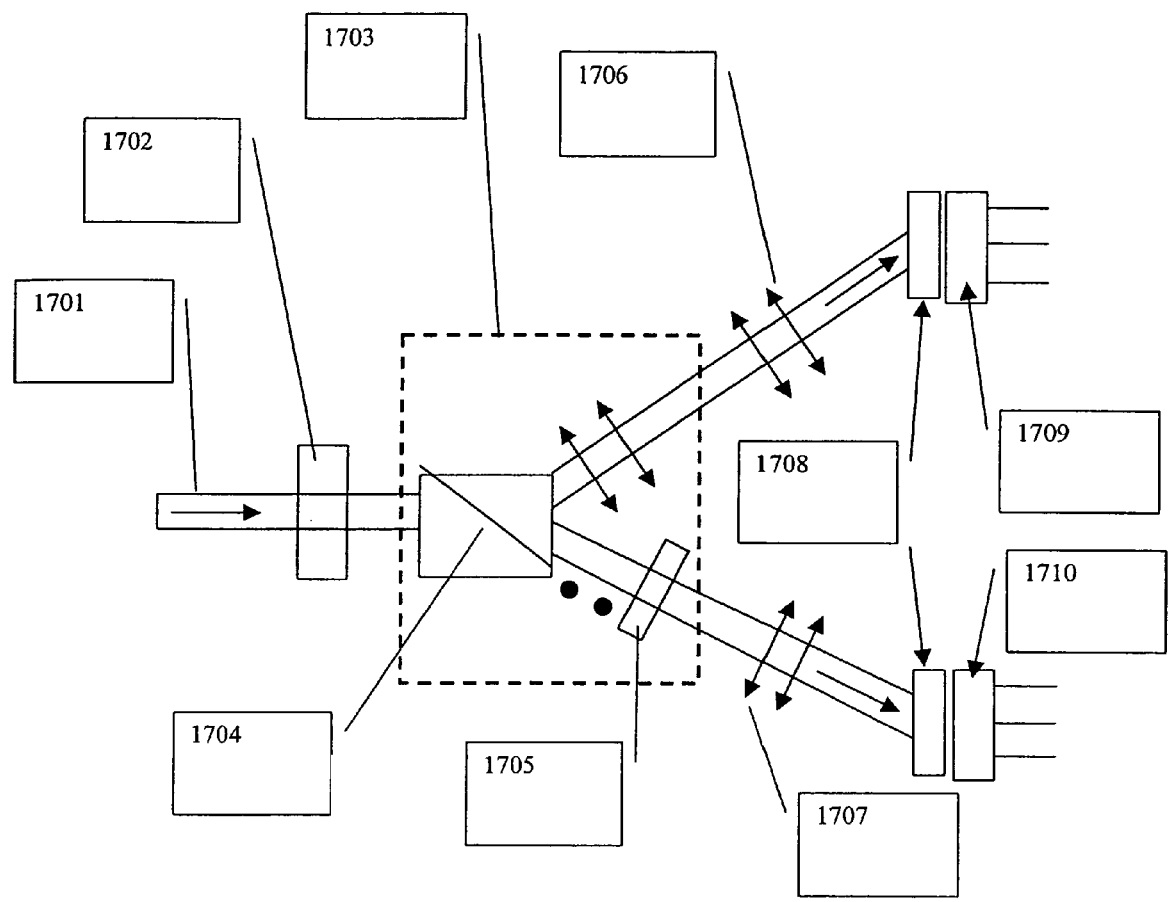
FIG. 17 is an illustration of a beam splitter that splits the beam into non-orthogonally polarized components that is capable of measuring phase shift of an elliptically polarized beam according to one embodiment of the present invention.

FIG. 17 illustrates the measurement of the phase shift of an elliptically polarized beam by the use of a beam splitter that splits the beam into non-orthogonally polarized components. The incoming elliptically polarized beam is labeled 1701, this beam is directed into a quarter wave plate 1702 and subsequently into a beam splitter 1703 which splits the beam into non-orthogonally polarized components. Internal to 1703 is a polarizing beam splitter such as a Wollaston prism 1704 or a polarizing cube beam splitter and a polarization rotation device 1705 such as a half wave plate or an optically active quartz polarization rotator. The two beams leaving the beam splitter 1703 are polarized in the same direction as indicated by 1706 and 1707. In general the two beams leaving the beam splitter 1703 may be polarized at any angle with respect to the other. This is accomplished by rotating a half wave plate 1705. (which is internal to the beam splitter 1703) to an arbitrary angle so that the beam leaving 1707 will now be polarized at an arbitrary angle with respect to beam 1706. After the beams leave the beam splitter 1703 they strike diffusers 1708 and subsequently are detected by photodetectors 1709 and 1710. The advantage of this type of beam splitter 1703 is that the outgoing beams may be polarized in the same direction. As a result when the beams 1706 and 1707 strike the diffusers 1708 and photodetectors 1709 and 1710 the reflection from these surfaces will be identical and the detected signals will have identical reduction due to surface reflection. This fact makes the calibration of the instrument considerably easier. The computation of the phase shift of the incoming beam 1701 is computed from the difference in the amplitude of the two beams as measured by the photodetectors 1709 and 1710.

The incoming laser beams discussed in previous paragraphs have been described as P, S or 45° polarized beams. These earlier discussions are preferred embodiments of this invention. It is also possible to illuminate the surface with unpolarized light and detect the resulting reflected signals with the same optical and electronic methods. The resulting detected signals, which use a source of light which is unpolarized, will still give measurements of the phase shift, topography, reflectivity, defects and particles.

While the invention has been particularly shown and described with reference to a preferred embodiment and several alternate embodiments, it will be understood by persons skilled in the relevant art that various changes in form and details can be made therein without departing from the spirit and scope of the invention.

What is claimed is:

1. A system for measuring a specular reflectivity of a light signal, comprising:
    a first light source for transmitting a first incident light signal toward a first surface of a first object in a first plane of incidence wherein said first object is at least on of a magnetic disk, a silicon wafer and a transparent glass substrate;
    a first polarization splitter for separating, from a first reflected light signal that has reflected off the first surface of said first object, a first mixed reflected polarized light signal component having a first phase and a second mixed reflected polarized light signal component having a second phase different from said first phase, wherein said first mixed reflected polarized light signal component comprises both P-polarized and S-polarized light relative to the plane of incidence of said first incident light signal, and wherein said second mixed reflected polarized light signal component comprises both P-polarized and S-polarized light relative to the plane of incidence of said first incident light signal;
    a first detector for detecting a first intensity of said firms mixed reflected polarized light signal component;
    a second detector for detecting a second intensity of said second mixed reflected polarized light signal component;
    a first spatial filter positioned to block a light signal reflected from a second surface of said first object from reaching said first and second detectors; and
    a first specular reflectivity determinator for determining a first specular reflectivity based upon said first and second intensitities.

2. The system of claim 1, wherein the first light source comprises a laser diode.

3. The system of claim 1, wherein the first polarization splitter comprises a quarter wave plate.

4. The system of claim 1, wherein the first polarization splitter comprises a Wollaston prism.

5. The system of claim 1, wherein the first detector and the second detector comprise a quadrant detector.

6. The system of claim 1, further comprising an integrating sphere, and wherein the first spatial filter is positioned adjacent the integrating sphere.

7. The system of claim 1, further comprising a processing device.

8. A method for measuring a specular reflectivity of a light signal, comprising the steps of
    transmitting a first incident light signal toward a first surface of a first object in a first plane of incidence wherein said first object is at least one of a magnetic disk, a silicon wafer and a transparent glass substrate;
    separating, from a first reflected light signal that has reflected off the first surface of said first object, a first mixed reflected polarized light signal component having a first phase and a second mixed reflected polarized light signal component having a second phase different from said first phase, wherein said first mixed reflected polarized light signal component comprises both P-polarized and S-polarized light relative to the plane of incidence of said first incident light signal, and wherein said second mixed reflected polarized light signal component comprises both P-polarized and S-polarized light relative to the plane of incidence of said first incident light signal;
    detecting a first intensity of said first mixed reflected polarized light signal component;
    detecting a second intensity of said second mixed reflected polarized light signal component; and
    determining a first specular reflectivity based upon said first and second intensities.

9. The method of claim 8, wherein transmitting a first incident light signal toward a first surface comprises activating a laser diode.

10. The method of claim 8, wherein separating, from a first reflected light signal that has reflected off the first surface of said first object, a first mixed reflected polarized light signal component having a first phase and a second mixed reflected polarized light signal component having a second phase different from said first phase, comprises passing the first reflected light signal through a Wollaston prism.

11. The method of claim 8, wherein determining a first specular reflectivity based upon said first and second intensities comprises summing the first intensity signal with a multiple of the second intensity signal.

12. The method of claim 8, further comprising determining a phase shift between the first mixed reflected polarized light signal component and the second mixed reflected polarized light signal component.

13. The method of claim 8, further comprising using the first mixed reflected polarized light signal component and the second mixed reflected polarized light signal component to determine a surface characteristic of the first object.

* * * * *